United States Patent [19]

Takeuchi et al.

[11] 4,347,308
[45] Aug. 31, 1982

[54] PHOTOGRAPHIC MATERIALS

[75] Inventors: Tetsuo Takeuchi, Fujinomiya; Yasuo Mukunoki; Junji Minanizono, both of Minami-ashigara, all of Japan

[73] Assignee: Fuji Photo Film Co., Ltd., Kanagawa, Japan

[21] Appl. No.: 235,223

[22] Filed: Feb. 17, 1981

[30] Foreign Application Priority Data

Feb. 15, 1980 [JP] Japan .................................. 55-18089
Feb. 15, 1980 [JP] Japan .................................. 55-18090

[51] Int. Cl.³ .......................... G03C 1/38; G03C 1/76; G03C 1/84; G03C 1/82
[52] U.S. Cl. ..................... 430/529; 430/631; 430/634; 430/635; 430/636; 430/961; 430/527
[58] Field of Search ............... 430/631, 633, 634, 635, 430/636, 961, 529, 527, 528

[56] References Cited

U.S. PATENT DOCUMENTS

| | | | |
|---|---|---|---|
| 2,240,476 | 4/1941 | Simmons et al. | 430/636 |
| 3,220,847 | 11/1965 | Knox et al. | 430/633 |
| 3,666,478 | 5/1972 | Groh | 430/635 |
| 3,753,716 | 8/1973 | Ishihara et al. | 430/529 |
| 3,754,924 | 8/1973 | DeGeest | 430/635 |
| 4,119,465 | 10/1978 | Matsuda et al. | 430/636 |
| 4,201,586 | 5/1980 | Hori | 430/631 |
| 4,242,444 | 12/1980 | Habu et al. | 430/635 |
| 4,267,265 | 5/1981 | Sugimoto et al. | 430/527 |

*Primary Examiner*—Mary F. Downey
*Attorney, Agent, or Firm*—Sughrue, Mion, Zinn, MacPeak & Seas

[57] ABSTRACT

A photographic material is described containing in at least one photographic layer a compound of formula (I)

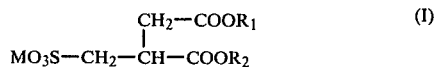

wherein at least one of $R_1$ and $R_2$ is a fluorine-substituted alkyl group, and $R_1$ or $R_2$ can be a substituted or unsubstituted alkyl or aryl group, and M is a cation.

21 Claims, No Drawings

PHOTOGRAPHIC MATERIALS

BACKGROUND OF THE INVENTION

This invention relates to a photographic material having an improved antistatic property, and more particularly, to a photographic material having an antistatic property that is retained over an extended period of time.

Photographic light-sensitive materials generally comprise an electrically insulative support and one or more photographic layers. Therefore, electrostatic charges often accumulate during the production of photographic light-sensitive materials or upon use thereof due to contact friction with, or delamination from, the surfaces of the same or different materials. This accumulation of electrostatic charge may result in several problems, the most serious of which is the formation of spots, or tree-like or fur-like lines upon development of exposed photographic films, due to the discharge of the accumulated electrostatic charge before development (since the discharge excites the light-sensitive layer). This is the so-called static marks, which seriously affects commercial value of photographic films and, in extreme cases, can completely destroy the commercial value. For example, it can readily be understood that such static marks on X-ray films for medical or industrial use could lead to an extremely dangerous misdiagnosis. This phenomenon is an extremely difficult problem, because it is only observed after development. In addition, the accumulated electrostatic charge can cause secondary problems, such as adhesion of dust to the film surface and non-uniform coating.

As is explained above, such electrostatic charges often accumulate upon production and use of photographic light-sensitive materials. In the production steps, the electrostatic charge develops due to contact friction between photographic films and rollers or separation of the support surface from the emulsion surface during the film-winding or film-unwinding. With finished products, it develops due to separation of a base surface and an emulsion surface from each other upon winding up and charging films, or contact or separation of X-ray films with or from mechanical members or fluorescent brightening paper in an automatic photographing machine.

Static marks in photographic light-sensitive materials formed by the accumulated electrostatic charge become a more serious problem as the sensitivity of the photographic light-sensitive materials increases and as the processing speed increases. Particularly, photographic light-sensitive materials have in more recent times often been subjected to severe processing conditions, e.g., to increase sensitivity high-speed coating, high-speed photographing, high-speed automatic processing, etc., and hence static marks have occurred more readily.

The best solution to the problem of static electricity is to increase the conductivity of the photographic materials, thus allowing the charge to dissipate in a short time prior to discharge of the accumulated charge.

Thus, attempts have been made to improve the conductivity of the support and various surface-coating layers of photographic light-sensitive materials using various hygroscopic materials, water-soluble inorganic salts, certain kinds of surfactants, polymers, etc. Thus, the polymers described, for example, in U.S. Pat. Nos. 2,882,157, 2,972,535, 3,062,785, 3,262,807, 3,514,291, 3,615,157, 3,753,716, 3,938,999, etc., the surfactants described, for example, in U.S. Pat. Nos. 2,982,651, 3,428,456, 3,457,076, 3,454,625, 3,552,972, 3,655,387, etc., and zinc oxide, semiconductors, colloidal silica, etc., described, for example, in U.S. Pat. Nos. 3,062,700, 3,245,833, and 3,525,621 have been used.

However, the property of these materials are rather specific, and depend so much upon the kind of the film support and the photographic composition, that while they provide good results with some particular film supports and photographic constituents (e.g., photographic emulsions), they are completely useless for preventing development of static electricity with other film supports and photographic constituents and, in some cases, exert a detrimental influence on the photographic properties. In particular, it has been extremely difficult to prevent development of electrostatic charge on a hydrophilic colloidal layer and, in many cases, there results an insufficient reduction in surface resistance under conditions of low humidity or adhesion between the photographic light-sensitive materials or between a photographic light-sensitive material and other material under a high temperature and high humidity conditions.

On the other hand, some materials cannot be used due to their detrimental influences on photographic properties such as sensitivity of the photographic emulsion, fog, graininess, sharpness, etc., in spite of their excellent antistatic effect. An example is polyethylene oxide series compounds, generally known to have an antistatic effect. For instance, polyethylene oxide series compounds, generally known to have an antistatic effect, often exert detrimental influences on photographic properties such as an increase of fog, desensitization, deterioration of graininess, etc. In particular, it has been difficult to effectively impart an antistatic property to light-sensitive materials having photographic emulsions on both sides of a support, such as X-ray sensitive materials for medical use, without detrimentally influencing the photographic properties.

Furthermore, most of the conventional antistatic photographic materials become less antistatic as time goes by, and it has been particularly difficult to establish a technique that provides a photographic material which retains the antistatic property over an extended period of time. Even compounds that are effective as an antistat interfere with the application of a photographic layer that contains the antistat. Because of this, in most cases, the provision of an antistatic property in a photographic material is extremely difficult to achieve, and a photographic material including an antistatic agent (antistat) may have limited utility.

SUMMARY OF THE INVENTION

One object of this invention is to provide a photographic material having an improved antistatic property without compromising the photographic characteristics.

Another object of this invention is to provide an antistatic photographic material wherein the time-dependent change of the antistatic property is minimized.

A further object of this invention is to provide an antistat that can be incorporated in various photographic coating solutions without comprising their property to form a uniform photographic layer.

A further object of this invention is to provide an antistatic photographic material that has low surface resistivity and small static buildup at low humidity (ca. 25% RH).

These objects of this invention can be achieved by incorporating in at least one photographic layer of a photographic material a compound of formula (I)

$$\begin{array}{c} CH_2-COOR_1 \\ | \\ MO_3S-CH_2-CH-COOR_2 \end{array} \quad (I)$$

wherein at least one of $R_1$ and $R_2$ is a fluorine-substituted alkyl group, and $R_1$ and $R_2$ can be a substituted or unsubstituted alkyl or aryl group, and M is a cation.

DETAILED DESCRIPTION OF THE INVENTION

When $R_1$ or $R_2$ in formula (I) is an alkyl group, the alkyl preferably has from 1 to 30, and particularly preferably from 2 to 20, carbon atoms. The alkyl may be a straight or branched chain or cyclic alkyl group. Examples of substituents that may be present on the alkyl include an alkoxy group, a halogen atom (e.g., chlorine or fluorine), an aryl group, an acyloxy group, and an aryloxy group. When $R_1$ or $R_2$ is an aryl group, the aryl group is preferably a phenyl or naphthyl group. Examples of substituents that may be present on the aryl include an alkyl group, an alkoxy group, an acyloxy group, and halogen atom (e.g., chlorine or fluorine). When $R_1$ or $R_2$ represents a fluorine-substituted alkyl group, the substituted alkyl group may be a fluorinated alkyl group of the formula $-(CH_2)_nC_mF_{2m+1}$, $-(CH_2)_n(CF_2)_mH$, $-(CH_2CH_2O)_{n1}(CH_2)_nC_mF_{2m+1}$, $-(CH_2CH_2O)_{n1}(CH_2)_n(CF_2)_mH$, $-(CH_2)_{n1}NHCO(CF_2)_mH$ or $-(CH_2)_{n1}NHCOC_mF_{2m+1}$ (wherein n is 0, 1 or 2, m is 1 to 12, and n1 is 1 to 4). In formula (I), M is a cation such as a hydrogen ion, an alkali metal ion, an alkaline earth metal ion, ammonium, or amine. Particularly preferred examples of M include $Na^+$, $K^+$, $Ca^{++}$, $NH_4^+$, $C_2H_5\text{-}NH_3^+$, $HN(C_2H_5)_3^+$, and $H_3NCH_2CH_2OH^+$.

The compound of the formula (I) is specifically illustrated by, but not limited to, the following examples:

$$\begin{array}{c} CH_2COOC_4H_9 \\ | \\ NaO_3S-CH_2-CH-COOCH_2(CF_2)_6H \end{array} \quad (I-1)$$

$$\begin{array}{c} C_2H_5 \\ | \\ CH_2-COO-CH_2-CH-C_4H_9 \\ | \\ NaO_3S-CH_2-CH-COOCH_2(CF_2)_7H \end{array} \quad (I-2)$$

$$\begin{array}{c} CH_2-COO-C_{12}H_{25} \\ | \\ NaO_3S-CH_2-CH-COOCH_2(CF_2)_7H \end{array} \quad (I-3)$$

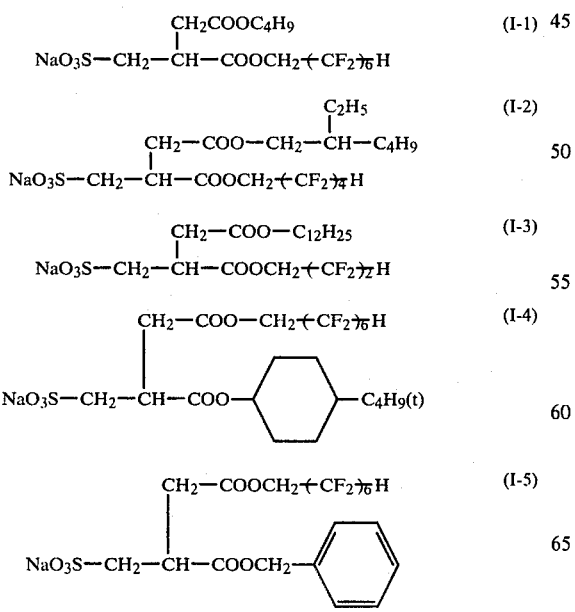

(I-4)

(I-5)

$$\begin{array}{c} CH_2-COO-CH_2(CF_2)_2H \\ | \\ NaO_3S-CH_2-CH-COO-CH_2(CF_2)_6H \end{array} \quad (I-6)$$

$$\begin{array}{c} CH_2-COOC_4H_9 \\ | \\ NaO_3S-CH_2-CH-COOCH_2CH_2NHCO(CF_2)_7H \end{array} \quad (I-7)$$

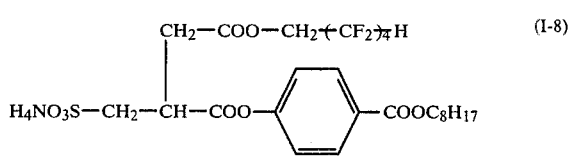

(I-8)

$$\begin{array}{c} CH_2-COOCH_2(CF_2)_6H \\ | \\ NaO_3S-CH_2-CH-COOCH_2(CF_2)_6H \end{array} \quad (I-9)$$

$$\begin{array}{c} CH_2-COO-CH_2(CF_2)_7H \\ | \\ NaO_3S-CH_2-CH-COO-C_{18}H_{37}(iso) \end{array} \quad (I-10)$$

$$\begin{array}{c} CH_2-COOC_{10}H_{21} \\ | \\ NaO_3S-CH_2-CH-COOCH_2(CF_2)_7H \end{array} \quad (I-11)$$

$$\begin{array}{c} CH_2-COOCH_2(CF_2)_6H \\ | \\ NaO_3S-CH_2-CH-COOCH_2CH-C_4H_9 \\ | \\ C_2H_5 \end{array} \quad (I-12)$$

$$\begin{array}{c} C_2H_5 \\ | \\ CH_2-COOCH_2CH-C_4H_9 \\ | \\ NaO_3S-CH_2-CH-COOCH_2CH_2C_4F_9 \end{array} \quad (I-13)$$

$$\begin{array}{c} CH_2-COOC_6H_{13} \\ | \\ NaO_3S-CH_2-CH-COOCH_2CH_2O-CH_2CH_2C_4F_9 \end{array} \quad (I-14)$$

Examples of methods of synthesizing the compounds of formula (I) are described hereunder.

SYNTHESIS EXAMPLE 1

Synthesis of Compound (I-11)

A mixture of 130.1 g of itaconic acid, 150.4 g of decyl alcohol and 1.5 g of p-toluenesulfonic acid in 200 ml of toluene was freed of 19.1 ml of water by heating under reflux for 8 hours. The reaction mixture was cooled and the precipitated crystal was filtered off (i.e., separated by filtration). The crystal was washed thoroughly with water and hexane to provide 128.8 g (yield=50.2%) of a monodecyl itaconic acid ester (m.p. 68.5°–69.5° C.).

The monoester (108.1 g) was reacted with 83.3 g of phosphorus pentachloride at room temperature for one hour. The by-product phosphorus oxychloride was distilled off under vacuum to obtain 124 g of an oily ester-acid chloride residue. The ester-acid chloride obtained (60.1 g) was added dropwise to a mixture of 75.7 g of dodecafluoroheptanol, 18 g of pyridine and 100 ml of chloroform at a temperature lower than 30° C. Following heating under reflux for 4.5 hours, the reaction mixture was cooled and washed with water and dilute aqueous sodium hydrogencarbonate. After distilling chloroform off, the residue was distilled under vacuum to provide 78.3 g of a fraction having a boiling point of 185°–195° C./2 mmHg (yield=64.4%).

A mixture of 60.1 g of the ester and 14.2 g of sodium hydrogensulfite in 14.2 g of water was heated under reflux for 15 hours. After the reaction, water was distilled off. The residue was dissolved in 300 ml of ethanol and the insoluble portion (inorganic matter) was removed to provide 65.8 g of the end compound (I-11).

SYNTHESIS EXAMPLE 2

Synthesis of Compound (I-12)

A mixture of 65.1 g of itaconic acid, 365.3 g of dodecafluoroheptanol and 1 g of p-toluenesulfonic acid in 100 ml of toluene was freed of 12 ml of water by heating under reflux for 24 hours. The reaction mixture was cooled and the precipitated crystal was filtered off. The crystal was washed with water and hexane to provide 106 g of a monoester of itaconic acid.

The monoester (88.8 g) was reacted with 41.7 g of phosphorus pentachloride at room temperature, followed by further reaction at 55° C. for 2 hours. The by-product phosphorus oxychloride was distilled off under vacuum to provide 92.5 g of an oily acid chloride product. The acid chloride obtained was added dropwise to a mixture of 26.0 g of 2-ethylhexanol and 15.8 g of pyridine in 100 ml of chloroform at a temperature lower than 40° C. Following heating under reflux for another 3 hours to complete the reaction, the reaction mixture was washed sequentially with water, dilute aqueous sodium bicarbonate, and water. Chloroform was distilled off and the residual oil obtained was distilled under vacuum to provide 69 g of an oily substance having a boiling point of 152°–160° C./2 mmHg.

A mixture of 64.0 g of the ester and 13.2 g of sodium hydrogensulfite in 20 ml of water was heated under reflux for 13 hours. After the reaction, water was distilled off, the wax residue was dissolved in 200 ml of benzene and the insoluble portion was filtered to obtain 64.0 g of the compound (I-12).

SYNTHESIS EXAMPLE 3

Synthesis of Compound (I-9)

A mixture of 35.5 g of itaconic acid, 230 g of dodecafluoroheptanol and 2 g of p-toluenesulfonic acid in 100 ml of toluene was freed of 4.5 ml of water by heating under reflux for 20 hours. The reaction mixture was washed sequentially with water, dilute aqueous caustic soda and water, freed of toluene by distillation, and subjected to distillation under vacuum to provide 105 g of an ester of itaconic acid having a boiling point of 165°–172° C./1.5 mmHg.

The ester (105 g) in 15 g of sodium hydrogensulfite and 20 ml of water was heated for 9 hours to form a homogeneous water-soluble solution. Thereafter, water was removed and the residue was dissolved in ethanol. By distilling off the insoluble portion and ethanol, 120 g of colorless wax, compound (I-9), was obtained.

SYNTHESIS EXAMPLE 4

Synthesis of Compound (I-13)

A mixture of 260.2 g of itaconic acid, 247.4 g of 2-ethylhexanol and 3 g of p-toluenesulfonic acid in 300 ml of toluene was freed of 38.4 ml of water by heating under reflux for 8.5 hours. After cooling, the insoluble portion was filtered off, the filtrate was washed with water and, then, toluene layer was separated. The oily residue (the toluene layer) was distilled under vacuum to provide 314 g (yield=68.2%) of an oily monoester having a boiling point of 158°–162° C./2 mmHg.

The monoester (266.5 g) was reacted with 229.1 g of phosphorus pentachloride at room temperature, and the by-product phosphorus oxychloride was distilled off under vacuum. Monoester-monocarboxylic acid chloride was obtained as an oily substance. The acid chloride obtained (57.1 g) was added dropwise to a mixture of 58.1 g of nonafluorohexanol, 22.3 g of triethylamine and 100 ml of chloroform at a temperature lower than 5° C. The mixture was heated first at room temperature for one hour, then at 70° C. for one hour. After cooling, the reaction mixture was sequentially washed with water, dilute aqueous caustic soda and water, and chloroform was distilled off. By distilling the residue under vacuum, 27.1 g of an ester having a boiling point of 148°–154° C./1-2 mmHg was obtained.

A mixture of 24.3 g of the ester, 5.5 g of sodium hydrogensulfite and 10 ml of water was heated at 100° C. for 7 hours. After cooling, the reaction mixture was dissolved in 10 ml of ethanol and washed with 50 ml of hexane three times. After distilling off ethanol and water, the residue was dissolved in 50 ml of ethanol and the insoluble portion was filtered off. The filtrate was evaporated to dryness under vacuum to provide 13.3 g of the compound (I-13).

The compounds of the formula (I) according to the present invention are added to at least one layer of the photographic light-sensitive material, preferably an outermost layer, such as a silver halide emulsion layer, a surface-protecting layer, an interlayer, a backing layer, an overcoat layer, etc. The silver halide emulsion layer and the interlayer can be an outermost layer, for example, during a preparation step of the photographic light-sensitive material. In particular, addition to a surface layer (an outermost layer) such as a surface-protecting layer, a backing layer and an overcoat layer is preferable.

In applying the compound of the formula (I) according to the present invention to a photographic light-sensitive material, the compound is dissolved in water, an organic solvent (e.g., methanol, isopropanol, acetone, etc.), or a mixture thereof, and added to a coating solution of a surface-protecting layer, a backing layer, an overcoat layer, or the like, followed by coating by dip-coating, air knife-coating, or extrusion coating using a hopper, e.g., as described in U.S. Pat. No. 2,681,294, alternatively, two or more layers may be coated at the same time according to methods described in U.S. Pat. Nos. 3,508,947, 2,941,898, 3,526,528, etc., or the material may be dipped in an antistatic agent solution. If desired, an antistatic solution containing the compounds of the present invention can be applied to the protective layer.

The compound of formula (I) according to the present invention is used in an amount of from 0.05 to 50 mg/m$^2$, and particularly desirably from 1 to 20 mg/m$^2$.

However, the amount may vary depending upon the kind of photographic film base used, the photographic composition, form, and the coating method.

When the compound of formula (I) according to the present invention is incorporated in at least one photographic layer of a photographic material in combination with an alkyl betaine surfactant, static buildup of a surface of the photographic material can be controlled and also surface resistivity thereof can be reduced. Thus, the combination use of the compound of formula (I) and the alkyl betaine surfactant is very preferred.

The alkyl betaine surfactant which is particularly effective is represented by formulae (II) or (III):

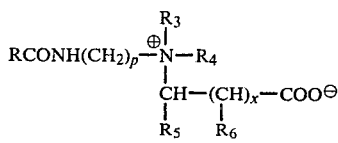 (II)

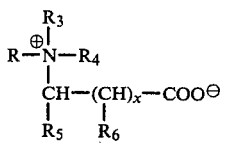 (III)

wherein R represents a saturated or unsaturated hydrocarbon group having from 7 to 21 carbon atoms; $R_3$ and $R_4$ each represents an alkyl group having from 1 to 18 carbon atoms, a hydroxyalkyl group, or a polyalkylene oxide group; $R_5$ and $R_6$ each represents hydrogen or an alkyl group having from 1 to 4 carbon atoms; p is an integer of at least 2; and x is 0 or 1. Particularly preferred compounds of formulae (II) and (III) are those in which R represents an alkyl group having from 11 to 17 carbon atoms, $R_3$ and $R_4$ each represents an alkyl group having 1 to 3 carbon atoms, $R_5$ and $R_6$ each represents hydrogen, p is 2 or 3, and x is 0 or 1.

Specific examples of the compound of formula (II) or (III) include the following:

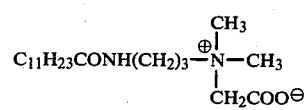 (II-1)

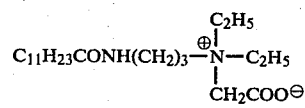 (II-2)

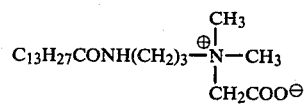 (II-3)

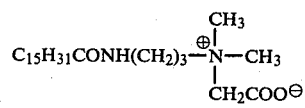 (II-4)

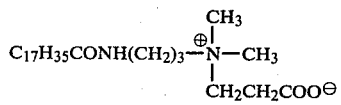 (II-5)

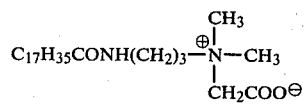 (II-6)

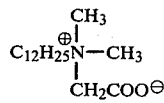 (III-1)

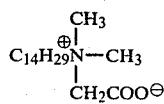 (III-2)

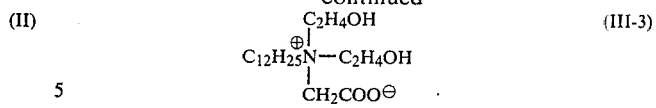 (III-3)

SYNTHESIS EXAMPLE 5

Synthesis of Compound (II-1)

A reactor was charged with 78 g of toluene, 5.4 g of triethylamine and 6 g of N,N-dimethylpropylenediamine, and the mixture was stirred at room temperature. To the mixture, there was added dropwise a mixture of 11.5 g of lauroyl chloride and 22 g of toluene at a temperature lower than 50° C. The mixture was heated at 60° C. under stirring for 30 minutes. After the heating, water was added to the reaction mixture and the insoluble salts were removed. By concentrating the toluene solution, a white solid having a melting point of 37° C. was removed in a yield of 99%. Identification by conventional methods showed that the solid was $C_{11}H_{23}CONH(CH_2)_3N(CH_3)_2$.

The intermediate thus-obtained (14.9 g) was dissolved in 7 g of methanol. Separately from the methanol solution, a mixture of 5 g of monochloroacetic acid and 6 g of methanol was prepared in a reactor. To the mixture, there was added dropwise 10.3 g of 28% aqueous sodium methylate, so that the temperature of the system did not exceed 40° C. The methanol solution of the intermediate was also added dropwise to the mixture and the overall mixture was heated at 70° C. for 7 hours under stirring. The mixture was freed of methanol under vacuum and concentrated to dryness. The concentrate was dissolved in 12.5 g of ethanol and the insoluble salts were removed. The residue was dissolved in 36 g of acetone, and the solution was filtered while heating. The filtrate was cooled to provide a white, water-soluble compound. The yield of the dried product was 15.2 g (85% of theoretical) and the melting point was 130°–135° C. The product was identified by conventional methods as compound (II-1).

When the compound of formula (I) alone is used, the amount thereof is from 0.05 to 50 mg/m² as described above. However, when the compound of formula (I) is used in combination with the alkyl betaine surfactant, it is preferred to use the compound of formula (I) in more amount than the above. That is, the fluorinated anionic surfactant of formula (I) is used preferably in an amount of from 5 to 100 mg/m², and particularly preferably from 20 to 50 mg/m², and the alkyl betaine surfactant is preferably used in an amount of from 10 to 500 mg/m², and particularly preferably from 30 to 100 mg/m².

The fluorinated anionic surfactant and the alkyl betaine surfactant are incorporated in at least one photographic layer of the photographic light-sensitive material, preferably an outermost layer, such as a silver halide emulsion layer, surface protective layer, interlayer, backing layer or an overcoat layer. The silver halide emulsion layer and the interlayer can be an outermost layer, for example, during a preparation step of the photographic light-sensitive material. They are preferably incorporated in a surface layer (an outermost layer) such as a surface protective layer, backing layer, or overcoat layer.

Materials used as the support for the light-sensitive material of the present invention include, for example, a cellulose nitrate film, a cellulose acetate film, a cellulose acetate butyrate film, a cellulose acetate propionate film, a polystyrene film, a polyethylene terephthalate film, a polycarbonate film, and laminates thereof. More particularly, examples include papers coated or laminated with baryta or α-olefin polymer, and in particular, a polymer of α-olefin containing from 2 to 10 carbon atoms such as polyethylene, polypropylene, ethylene-butane copolymer, etc.

The layers constituting the photographic light-sensitive materials of the present invention can contain various binders. For example, hydrophilic colloid binders include proteins (e.g., gelatin, colloidal albumin, casein, etc.), cellulose derivatives (e.g., carboxymethyl cellulose, hydroxyethyl cellulose, etc.), sugar derivatives (e.g., agar-agar, sodium alginate, starch derivatives, etc.), and synthetic hydrophilic colloids (e.g., polyvinyl alcohol, poly-N-vinyl pyrrolidone, polyacrylic acid copolymer, polyacrylamide, and derivatives or partially hydrolyzed products thereof). If desired, a mixture of two or more of these colloids can be used. Of these, the most generally used is gelatin. Gelatin as used herein means so-called lime-processed gelatin, acid-processed gelatin, and enzyme-processed gelatin.

The silver halide emulsion used in the present invention is usually prepared by mixing a solution of water-soluble silver salt (e.g., silver nitrate, etc.) with a solution of water-soluble halide (e.g., potassium bromide, etc.) in the presence of a solution of a water-soluble high polymer such as gelatin. As the silver halide, mixed silver halides such as silver chlorobromide, silver bromoiodide, silver chlorobromoiodide, etc., can be used as well as silver chloride and silver bromide.

The silver halide grains can be heat-treated in the presence of a chemical sensitizing agent (for example, sodium thiosulfate, N,N,N'-trimethylthiourea, monovalent gold thiocyanato complex, monovalent gold thiosulfato complex, stannous chloride, hexamethylenetetramine, etc.) to raise sensitivity without making the grain coarse.

The photographic emulsion can be subjected, if desired, to spectral sensitization or supersensitization by using polymethine sensitizing dyes (e.g., cyanine, merocyanine, carbocyanine, etc.), alone or in combination, or in further combination with styryl dye or the like.

To the photographic emulsion of the light-sensitive material of the present invention various compounds can be added in order to prevent reduction in sensitivity and formation of fog in the production step, during storage or during processing of the light-sensitive material. As such compounds, there have been long known extremely many compounds such as many heterocyclic compounds including 4-hydroxy-6-methyl-1,3,3a,7-tetrazaindene-3-methyl-benzothiazole and 1-phenyl-5-mercaptotetrazole, mercury-containing compounds, mercapto compounds, metal salts, and the like.

Some examples of usable compounds are described in C. E. K. Mees & T. H. James, *The Theory of the Photographic Process* (3rd Ed., 1966) citing original literature.

The photographic coupler that can be used in the photographic material of this invention includes compounds that are capable of developing a color upon oxidative coupling with an aromatic primary amine developer (e.g., phenylenediamine derivative or aminophenol derivative) in color developing process; magenta couplers such as 5-pyrazolone coupler, pyrazolobenzimidazole coupler, cyanoacetylcumarone coupler, and open acylacetonitrile coupler; yellow couplers such as acylacetamide coupler (e.g., benzoylacetanilides and pivaloylacetanilides); and cyan couplers such as naphthol coupler and phenol coupler.

The photographic material of this invention may contain an antifogging agent such as a hydroquinone derivative, aminophenol derivative, gallic acid derivative and ascorbic acid derivative.

The compound of formula (I) can be used in combination with a higher alcohol. Examples of the higher alcohol include amyl alcohol, cyclohexanol, octanol, cetyl alcohol and stearyl alcohol.

The photographic material of this invention may also contain an anti-discoloration agent such as a hydroquinone derivative, gallic acid derivative, p-alkoxyphenol, p-oxyphenol derivative and bisphenol.

The photographic material of this invention may contain a gelatin hardener which is selected from among many known compounds.

Typical examples of the hardeners include aldehyde compounds such as mucochloric acid, formaldehyde, trimethylolmelamine, glyoxal, 2,3-dihydroxy-1,4-dioxane, 2,3-dihydroxy-5-methyl-1,4-dioxane, succinaldehyde, glutaraldehyde, etc.; active vinyl compounds such as divinylsulfone, methylenebismaleimide, 1,3,5-triacryloylhexahydro-s-triazine, 1,3,5-trivinylsulfonylhexahydro-s-triazine, 1,3-bis(vinylsulfonylmethyl)-propanol-2, bis(α-vinylsulfonylacetamido)ethane, etc.; active halogen compounds such as 2,4-dichloro-6-hydroxy-s-triazine sodium salt, 2,4-dichloro-6-methoxy-s-triazine, etc.; ethyleneimine compounds such as 2,4,6-triethyleneimino-s-triazine, etc.; and the like.

To the layers constituting the photographic material of the present invention may be added surface active agents alone or in combination. They are generally used as coating aids but, in some cases, they are applied for other purposes, e.g., for the improvement of emulsion dispersion, sensitization, and other photographic properties, and adjustment of charging properties.

These surface active agents are classified into the following groups: natural surface active agents such as saponin; nonionic surface active agents such as polyalkylene oxide series, glycerin series, glycidol series ones, etc.; cationic surface active agents such as higher alkylamines, quaternary ammonium salts, heterocyclic compounds (e.g., pyridine, etc.), phosphonium compounds, sulfonium compounds, etc.; anionic surface active agents having an acidic group such as a carboxylic acid group, a sulfonic acid group, a phosphoric acid group, a sulfuric ester group, a phosphoric acid ester group, etc.; and amphoteric surface active agents such as aminoacids, aminosulfonic acids, aminoalcohol sulfuric or phorphoric esters, etc.

Examples of suitable surface active agents are described, for example, in patents such as U.S. Pat. Nos. 2,271,623, 2,240,472, 2,288,226, 2,739,891, 3,158,484, 3,201,253, 3,294,540, 3,415,649, 3,441,413, 3,442,654, 3,545,974, 3,666,478, 3,507,660, British Pat. No. 1,198,450, and so forth.

The photographic light-sensitive material of the present invention can contain in the light-sensitive material constituting layers thereof modified silicone and the like lubricating compositions, such as those described in U.S. Pat. Nos. 3,079,837, 3,080,317, 3,545,970 and 3,297,537 and Japanese Patent Application No. 129520/77.

The photographic light-sensitive material of the present invention can also contain in the light-sensitive material-constituting layers thereof a polymer latex, as described in U.S. Pat. Nos. 3,411,911, 3,411,912, Japanese Patent Publication No. 5331/70, etc., and a matting agent such as silica, strontium sulfate, barium sulfate, polymethyl methacrylate, and so forth.

The photographic material of the present invention substantially reduces problems due to static electricity developing during production steps and/or upon use of photographic light-sensitive materials.

More particularly, formation of static marks caused by contact between the emulsion surface of the photographic light-sensitive material and the back side thereof, contact between the emulsion surfaces, and contact between the photographic light-sensitive material and substances with which the light-sensitive material generally often comes into contact, such as rubber, metal, plastics, and fluorescent brightening paper, is remarkably reduced by the practice of the present invention.

Surprisingly enough, as will be shown by the following examples, incorporation of the compound of the present invention in an outermost layer of a photographic light-sensitive material results in remarkable reduction in surface resistance with virtually no adverse influences on photographic properties.

The present invention will now be described in more detail by the following examples which, however, do not limit the present invention.

EXAMPLE 1

Samples (1) to (8) each composed of a lamination of, in the order: a protective layer, an emulsion layer, a polyethylene terephthalate film base, an emulsion layer and a protective layer, were prepared by a conventional application and drying technique. The compositions of the respective layers are indicated below.

Emulsion Layer

Binder: gelatin 2.5 g/m$^2$
Amount of coated silver: 5 g/m$^2$
Composition of silver halide: AgI 1.5 mol% + AgBr 98.5 mol%
Hardener: chromium alum 0.8 g/100 g binder
Antifogging agent: 1-phenyl-5-mercaptotetrazole 0.5 g/100 g Ag Protective Layer Binder: gelatin 1.7 g/m$^2$ + potassium salt of sulfonated polystyrene (av. m.w. = ca. 70,000) 0.3 g/m$^2$
Hardener: sodium salt of 2-hydroxy-4,6-dichloro-s-triazine 0.4 g/100 g binder
Antistat: For the type of antistat and the amount used, see Table 1.

The compounds of formula (I) indicated in Table 1, saponin, and a fluorinated sulfosuccinic acid compound of the type described in Japanese Patent Application (OPI) No. 32322/76 (the term "OPI" as used herein refers to a "published unexamined Japanese patent application") were incorporated in the protective layers in the amounts indicated in Table 1. The resulting photographic films were left to stand at 25° C. and 25% RH (relative humidity) for 2 hours. Then, static marking on each film was measured by the method described below. Static Marking:

A white rubber sheet was placed on a surface of the sample and a rubber roller was rolled on the rubber sheet to apply a constant friction. After removing the rubber sheet, the sample was developed, fixed, and washed, and checked for the formation of static marks.

The results of the test for each sample are set forth in Table 1.

TABLE 1

| Sample No. | Antistat | Amount Added (mg/m$^2$) | Static Mark Just after Application | Static Mark 3 Months Later |
|---|---|---|---|---|
| 1 (control) | — | — | E | E |
| 2 (this invention) | Compound I-2 | 5 | A | A |
| 3 (this invention) | Compound I-2 | 10 | A | A |
| 4 (this invention) | Compound I-5 | 5 | A | A |
| 5 (this invention) | Compound I-10 | 5 | A | A |
| 6 (comparison) | Saponin | 100 | D | D |
| 7 (comparison) | Comparison* Compound | 5 | B | C |
| 8 (comparison) | Comparison* Compound | 10 | B | C |

*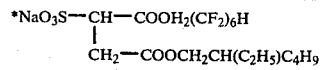
    |
    CH$_2$—COOCH$_2$CH(C$_2$H$_5$)C$_4$H$_9$

The static marking was evaluated on a 5-grade basis:
A: No static marks were observed.
B: Static marks were slightly observed.
C: Static marks were considerably observed.
D: Static marks were seriously observed.
E: Static marks were observed all over the surface.

The data in Table 1 shows that the photographic films which contain the fluorinated sulfoitaconic acid surfactant of this invention in the protective layers have improved antistatic property, and no static marks develop on the films. In addition, the films retain the good antistatic property for an extended period of time.

EXAMPLE 2

Samples (11) to (13) each composed of a lamination of, in the order: a triacetyl cellulose base, an antihalation layer, a red-sensitive layer, an interlayer, a green-sensitive layer, a yellow filter layer, a blue-sensitive layer and a protective layer, were prepared by a conventional application and drying technique. The compositions of the respective layers are indicated below.

Antihalation Layer

Binder: gelatin 4.4 g/m$^2$
Hardener: 1,3-bis(vinylsulfonyl)propanol-2 1.2 g/100 g binder
Coating aid: sodium dodecylbenzenesulfonate 4 mg/m$^2$
Ingredient of antihalation: black colloidal silver 0.4 g/m$^2$ Red-Sensitive Layer Binder: gelatin 7 g/m$^2$
Hardener: 1,3-bis(vinylsulfonyl)propanol-2 1.2 g/100 g binder
Coating aid: sodium dodecylbenzenesulfonate 10 mg/m$^2$
Amount of coated silver: 3.1 g/m$^2$
Composition of silver halide: AgI 2 mol% + AgBr 98 mol%

Antifogging agent: 4-hydroxy-6-methyl-1,3,3a,7-tetrazaindene 0.9 g/100 g Ag
Coupler: 1-hydroxy-4-(2-acetylphenyl)azo-N-[4-(2,4-di-tert-amylphenoxy)butyl]-2-naphthoamide 38 g/100 g Ag
Sensitizing dye: pyridinium salt of anhydro-5,5'-dichloro-9-ethyl-3,3'-di(3-sulfopropyl)thiacarbocyanine hydroxide 0.3 g/100 g Ag Interlayer Binder: gelatin 2.6 g/m$^2$
Hardener: 1,3-bis(vinylsulfonyl)propanol-2 1.2 g/100 g binder
Coating aid: sodium dodecylbenzenesulfonate 12 mg/m$^2$ Green-Sensitive Layer Binder: gelatin 6.4 g/m$^2$
Hardener: 1,3-bis(vinylsulfonyl)propanol-2 1.2 g/100 g binder
Coating aid: sodium dodecylbenzenesulfonate 9 mg/m$^2$
Amount of coated silver: 2.2 g/m$^2$
Composition of silver halide: AgI 3.3 mol% + AgBr 96.7 mol%
Stabilizer: 4-hydroxy-6-methyl-1,3,3a,7-tetrazaindene 0.6 g/100 g Ag
Coupler: 1-(2,4,6-trichlorophenyl)-3-[3-(2,4-di-tert-amylphenoxy)acetamido]benzamido-4-(4-methoxyphenyl)azo-5-pyrazolone 37 g/100 g Ag
Sensitizing dye: pyridinium salt of anhydro-5,5'-diphenyl-9-ethyl-3,3'-di(2-sulfoethyl)oxacarbocyaninehydroxide 0.3 g/100 g Ag Yellow Filter Layer Binder: gelatin 2.3 g/m$^2$
Filter component: yellow colloidal silver 0.7 g/m$^2$
Hardener: 1,3-bis(vinylsulfonyl)propanol-2 1.2 g/100 g binder
Surfactant: sodium salt of bis(2-ethylhexyl)succinate-2-sulfonic acid 7 mg/m$^2$ Blue-Sensitive Layer Binder: gelatin 7 g/m$^2$
Hardener: 1,3-bis(vinylsulfonyl)propanol-2 1.2 g/100 g binder
Coating aid: sodium dodecylbenzenesulfonate 8 mg/m$^2$
Amount of coated silver: 2.2 g/m$^2$
Composition of silver halide: AgI 3.3 mol% + AgBr 96.7 mol%
Stabilizer: 4-hydroxy-6-methyl-1,3,3a,7-tetrazaindene 0.4 g/100 g Ag
Coupler: 2'-chloro-5'-[2-(2,4-di-tert-amylphenoxy)butyramido]-α-(5,5'-dimethyl-2,4-dioxo-3-oxazolidinyl)-α-(4-methoxybenzoyl)acetanilide 45 g/100 g Ag Protective Layer Binder: gelatin 2 g/m$^2$ + styrene/maleic anhydride (1:1) copolymer (av. m.w. = ca. 100,000) 0.3 g/m$^2$
Hardener: 1,3-bis(vinylsulfonyl)propanol-2 1.2 g/100 g binder
Coating aid: sodium dioctylsulfosuccinate 5 mg/m$^2$ Sample 11 was comprised of the formulation described above. Sample 12 was the same as Sample 11 except that the protective layer contained 5 mg/m$^2$ of Compound (I-2). Sample 13 was the same as Sample 11 except that the protective layer contained 5 mg/m$^2$ of the fluorinated sulfosuccinic acid compound used in Samples 7 and 8 prepared in Example 1.

The antistatic properties of the samples were determined as in Example 1 and the results are set forth in Table 2 below.

TABLE 2

| | Comparison of Antistatic Property | | |
|---|---|---|---|
| | Sample No. | | |
| Results | (11) (control) | (12) (this invention) | (13) (comparison) |
| Static marking on fresh film | E | A | B |
| Static marking on 3 months old film | E | A | D |

Table 2 shows that the film containing the fluorinated sulfoitaconic acid surfactant of this invention in a protective layer has a significantly improved antistatic property. In addition, such good antistatic property is not lost upon storage.

EXAMPLE 3

To a subbed polyethylene terephthalate film base, a photographic emulsion coating solution comprising a stabilizer and hardener incorporated in an X-ray photographic high-sensitivity emulsion containing 6% gelatin and 6% silver iodobromide (silver iodide: 1.5 mol%), and an aqueous coating solution for forming surface protective layer that consisted of gelatin, water and a hardener and being free of an antistat were applied continuously and dried. For the compositions of the respective layers, see Table 3 below. The sample obtained was divided into four portions which were separately immersed in 3% aqueous solutions of the compounds shown in Table 4 for 30 minutes. As a comparison, one of the samples was immersed in 3% aqueous saponin, and another was immersed in 3% aqueous solution of fluorinated sulfosuccinic acid compound used in Example 1. The thus-treated samples were left to stand at 25° C. and 25% RH for 2 hours. Static marking was checked as follows: a white rubber sheet was placed on a face of the sample and a rubber roller was rolled on the rubber sheet at 25° C. and 40% RH to apply a constant friction. After removing the rubber sheet, the sample was developed in a developer of the formulation indicated below, and fixed for checking the formation of static marks. The results of the test with each sample are set forth in Table 4.

| Formulation of Developer | |
|---|---|
| Warm water (50° C.) | 700 ml |
| N—Methyl-p-aminophenol sulfate | 4 g |
| Anhydrous sodium sulfite | 60 g |
| Hydroquinone | 10 g |
| Sodium carbonate (monohydrate) | 53 g |
| Potassium bromide | 25 g |
| Water to make | 1 l |

TABLE 3

| Composition of Coating Solution (per kg) | | |
|---|---|---|
| | For Emulsion Layer | For Protective Layer |
| Binder | Gelatin 60 g | Gelatin 50 g |
| Silver | Silver iodobromide 60 g | — |
| Hardener | 2% Solution of Na | 2% Solution of Na |

TABLE 3-continued

| | Composition of Coating Solution (per kg) | |
|---|---|---|
| | For Emulsion Layer | For Protective Layer |
| Stabilizer | salt of 2-hydroxy-4,6-dichloro-s-triazine 10 ml<br>0.3% Solution of 1-phenyl-5-mercaptotetrazole 7 ml | salt of 2-hydroxy-4,6-dichloro-s-triazine 10 ml<br>— |
| Water | 880 ml | 950 ml |

(thickness: emulsion layer: 5μ, protective layer: 1μ)

TABLE 4

| | Comparison of Antistatic Property | |
|---|---|---|
| Sample No. | Antistat | Static Marking* |
| 21 (this invention) | Compound (I-13) | A (A) |
| 22 (comparison) | Comparison Compound | B (C) |
| 23 (comparison) | Saponin | C (C) |
| 24 (control) | None | D (D) |

*The letters in parentheses indicate the results observed 3 months later.

As Table 4 shows, no static marks were formed on Sample 21 treated with an aqueous solution containing the fluorinated itaconic surfactant of this invention, and the antistatic property of the film decreased little upon storage for 3 months. The performance of Sample 22 that was treated with an aqueous solution containing the fluorinated sulfosuccinic acid described in Japanese Patent Application (OPI) No. 32322/76 was only a little inferior to that of Sample 21, but upon storage for 3 months, its antistatic property lowered greatly and a great number of static marks were formed.

EXAMPLE 4

Samples (101) to (112), each composed of a lamination of, in the order: a protective layer, an emulsion layer, a polyethylene terephthalate film base, an emulsion layer, and a protective layer, were prepared by a conventional application and drying technique. The compositions of the respective layers are indicated below.

Emulsion Layer

Binder: gelatin 2.5 g/m²

Amount of coated silver: 5 g/m²
Composition of silver halide: AgI 1.5 mol% + AgBr 98.5 mol%
Hardener: chromium alum 0.8 g/100 g binder
Antifogging agent: 1-phenyl-5-mercaptotetrazole 0.5 g/100 g Ag Protective Layer Binder: gelatin 1.7 g/m²
Hardener: sodium salt of 2-hydroxy-4,6-dichloro-s-triazine 0.4 g/100 g binder
Matting agent: polymethyl methacrylate (av. particle size=5μ) 25 mg/m²

The alkyl betaine compounds, fluorinated anionic compounds of formula (I) indicated in Table 5, and saponin (for comparison) were incorporated in the protective layers in the amounts indicated in Table 5. The resulting photographic films were left to stand at 25° C. and 25% RH (relative humidity) for 2 hours. Then, the surface resistivity, static buildup and static marking properties of each film were measured by the methods described below. Samples (108) to (110) contained fluorinated compound as described in Japanese Patent Publication No. 39291/77.

(a) Surface Resistivity

The sample was sandwiched between brass electrodes (electrode gap: 0.14 cm; length: 10 cm; the part in contact with the sample was made of stainless steel), the one-minute value was read on an electrometer (TR-8651 of Takeda Riken), and the surface resistivity was calculated by Ohm's Law. The smaller the surface resistivity, the better the antistatic property.

(b) Static Buildup

A rubber/stainless steel roller was rolled on a sample (3 cm×30 cm) under a load of 7 kg and at a rate of 125 m/minute, and the resulting static buildup was measured with a Faraday cage.

(c) Static Marking

A white rubber sheet was placed on a surface of the sample and a rubber roller was rolled on the rubber sheet to apply a constant friction. After removing the rubber sheet, the sample was developed, fixed, washed, and checked for the formation of static marks.

The results of the three tests for each sample are set forth in Table 5.

TABLE 5

| Sample | Antistat | | | | Measurements** | | |
|---|---|---|---|---|---|---|---|
| | Component 1 | Amount (mg/m²) | Component 2 | Amount (mg/m²) | Surface Resistivity (Ω) | Static Buildup (in coulombs) | Static Marking |
| 101 (control) | Compound II-1 | 50 | None | — | $5.0 \times 10^{13}$ ($8.0 \times 10^{13}$) | $9.5 \times 10^{-8}$ ($1.3 \times 10^{-7}$) | D (E) |
| 102 (this invention) | Compound II-1 | 50 | I-2 | 10 | $1.0 \times 10^{13}$ ($2.2 \times 10^{13}$) | $2.4 \times 10^{-8}$ ($2.6 \times 10^{-8}$) | B (B) |
| 103 (this invention) | Compound II-1 | 50 | Compound I-2 | 20 | $5.1 \times 10^{12}$ ($5.5 \times 10^{12}$) | $1.6 \times 10^{-8}$ ($1.9 \times 10^{-8}$) | A (A) |
| 104 (this invention) | Compound II-1 | 50 | Compound I-2 | 30 | $2.7 \times 10^{12}$ ($3.0 \times 10^{12}$) | $7.5 \times 10^{-9}$ ($9.0 \times 10^{-9}$) | A (A) |
| 105 (this invention) | Compound II-1 | 50 | Compound I-2 | 40 | $3.0 \times 10^{12}$ ($3.5 \times 10^{12}$) | $1.2 \times 10^{-8}$ ($1.5 \times 10^{-8}$) | A (A) |
| 106 (this invention) | Compound II-1 | 50 | Compound I-8 | 30 | $3.4 \times 10^{12}$ ($3.5 \times 10^{12}$) | $1.2 \times 10^{-8}$ ($2.0 \times 10^{-8}$) | A (A) |
| 107 | Compound | | Compound | | | | |

TABLE 5-continued

| Sample | Antistat Component 1 | Amount (mg/m$^2$) | Component 2 | Amount (mg/m$^2$) | Measurements** Surface Resistivity (Ω) | Static Buildup (in coulombs) | Static Marking |
|---|---|---|---|---|---|---|---|
| (this invention) 108 | II-1 | 50 | I-13 | 30 | $3.0 \times 10^{12}$ ($3.7 \times 10^{12}$) | $9.9 \times 10^{-9}$ ($1.5 \times 10^{-8}$) | A (A) |
| (comparison) 109 | Compound II-1 | 50 | Comparison* Compound | 10 | $5.5 \times 10^{13}$ ($8.0 \times 10^{13}$) | $-6.0 \times 10^{-8}$ ($-3.1 \times 10^{-8}$) | D (D) |
| (comparison) 110 | Compound II-1 | 50 | Comparison* Compound | 30 | $5.7 \times 10^{13}$ ($8.1 \times 10^{13}$) | $-1.5 \times 10^{-7}$ ($-9.0 \times 10^{-8}$) | E (E) |
| (comparison) 111 | Compound II-1 | 50 | Comparison* Compound | 40 | $5.4 \times 10^{13}$ ($8.7 \times 10^{13}$) | $-1.0 \times 10^{-7}$ ($-1.0 \times 10^{-7}$) | E (E) |
| (comparison) 112 | Saponin | 50 | None | — | $2.0 \times 10^{14}$ ($2.0 \times 10^{14}$) | $1.2 \times 10^{-7}$ ($1.2 \times 10^{-7}$) | D (D) |
| (control) | None | — | None | — | $2.1 \times 10^{14}$ ($2.0 \times 10^{14}$) | $9.9 \times 10^{-8}$ ($9.9 \times 10^{-8}$) | E (E) |

*$C_8F_{17}SO_2N(C_2H_5)CH_2COOK$
**The figures or letters in parentheses indicate the measurements obtained 3 months later.

The static marking was evaluated on a 5-grade basis:
A: No static marks were observed.
B: Static marks were slightly observed.
C: Static marks were considerably observed.
D: Static marks were seriously observed.
E: Static marks were observed all over the surface.

The data in Table 5 shows that the photographic films which contain both the alkyl betaine compound and the fluorinated surfactant of this invention in the protective layers have significantly reduced surface resistivity and static buildup, and hence a better antistatic property. In addition, the films retain the good antistatic property for an extended period of time. In the films using the fluorinated compound described in Japanese Patent Publication No. 39291/77, the surface resistivity was reduced in some extent but not sufficient, and a slight change in the amount of the compound added resulted in a great change in the triboelectric charge.

EXAMPLE 5

Samples (121) to (124), each composed of a lamination of, in the order: a triacetyl cellulose base, an antihalation layer, a red-sensitive layer, an interlayer, a green-sensitive layer, a yellow filter layer, a blue-sensitive layer, and a protective layer, were prepared by a conventional application and drying technique. The compositions of the respective layers are indicated below.

Antihalation Layer

Binder: gelatin 4.4 g/m$^2$
Hardener: 1,3-bis(vinylsulfonyl)propanol-2 1.2 g/100 g binder
Coating aid: sodium dodecylbenzenesulfonate 4 mg/m$^2$
Ingredient of antihalation: black colloidal silver 0.4 g/m$^2$ Red-Sensitive Layer Binder: gelatin 7 g/m$^2$
Hardener: 1,3-bis(vinylsulfonyl)propanol-2 1.2 g/100 g binder
Coating aid: sodium dodecylbenzenesulfonate 10 mg/m$^2$
Amount of coated silver: 3.1 g/m$^2$
Composition of silver halide: AgI 2 mol% + AgBr 98 mol%
Antifogging agent: 4-hydroxy-6-methyl-1,3,3a,7-tetrazaindene 0.9 g/100 g Ag
Coupler: 1-hydroxy-4-(2-acetylphenyl)azo-N-[4-(2,4-ditert-amylphenoxy)butyl]-2-naphthoamide 38 g/100 g Ag
Sensitizing dye: pyridinium salt of anhydro-5,5'-dichloro-9-ethyl-3,3'-di(3-sulfopropyl)thiacarbocyanine hydroxide 0.3 g/100 g Ag Interlayer Binder: gelatin 2.6 g/m$^2$
Hardener: 1,3-bis(vinylsulfonyl)propanol-2 1.2 g/100 g binder
Coating aid: sodium dodecylbenzenesulfonate 12 mg/m$^2$ Green-Sensitive Layer Binder: gelatin 6.4 g/m$^2$
Hardener: 1,3-bis(vinylsulfonyl)propanol-2 1.2 g/100 g binder
Coating aid: sodium dodecylbenzenesulfonate 9 mg/m$^2$
Amount of coated silver: 2.2 g/m$^2$
Composition of silver halide: AgI 3.3 mol% + AgBr 96.7 mol%
Stabilizer: 4-hydroxy-6-methyl-1,3,3a,7-tetrazaindene 0.6 g/100 g Ag
Coupler: 1-(2,4,6-trichlorophenyl)-3-[3-(2,4-di-tertamylphenoxy)acetamido]benzamido-4-(4-methoxyphenyl)azo-5-pyrazolone 37 g/100 g Ag
Sensitizing dye: pyridinium salt of anhydro-5,5'-diphenyl-9-ethyl-3,3'-di(2-sulfoethyl)oxacarbocyanine hydroxide 0.3 g/100 g Ag Yellow Filter Layer Binder: gelatin 2.3 g/m$^2$
Filter component: yellow colloidal silver 0.7 g/m$^2$
Hardener: 1,3-bis(vinylsulfonyl)propanol-2 1.2 g/100 g binder
Surfactant: sodium salt of bis(2-ethylhexyl)succinate-2-sulfonic acid 7 mg/m$^2$ Blue-Sensitive Layer Binder: gelatin 7 g/m$^2$
Hardener: 1,3-bis(vinylsulfonyl)propanol-2 1.2 g/100 g binder
Coating aid: sodium dodecylbenzenesulfonate 8 mg/m$^2$
Amount of coated silver: 2.2 g/m$^2$
Composition of silver halide: AgI 3.3 mol% + AgBr 96.7 mol%
Stabilizer: 4-hydroxy-6-methyl-1,3,3a,7-tetrazaindene 0.4 g/100 g Ag
Coupler: 2'-chloro-5'-[2-(2,4-di-tert-amylphenoxy)-butyramido]-α-(5,5'-dimethyl-2,4-dioxo-3-oxazolidinyl)-α-(4-methoxybenzoyl)acetanilide 45 g/100 g Ag

Protective Layer

Binder: gelatin 2 g/m²
Hardener: 1,3-bis(vinylsulfonyl)propanol-2 1.2 g/100 g binder
Matting agent: polymethyl methacrylate (av. particle size=ca. 5μ) 20 mg/m²
Coating aid: sodium dioctylsulfosuccinate 5 mg/m²

Sample (121) constituted the formulation exactly as described above. Sample (122) was the same as Sample (121), except that the protective layer contained 50 mg/m² of the alkyl betaine compound (II-1). Sample (123) was the same as Sample (121) except that the protective layer contained 50 mg/m² of the alkyl betaine compound (II-1) and 40 mg/m² of the Compound (I-3). Sample (124) was the same as Sample (121) except that the protective layer contained 50 mg/m² of the Compound (II-2) and 40 mg/m² of the Compound (I-5).

The antistatic properties of the samples were determined as in Example 4, and the results are set forth in Table 6 below.

TABLE 6

| Sample No. | Antistat | | Antistatic Property | |
|---|---|---|---|---|
| | | | Surface Resistivity (Ω) | Static Marking |
| 121 (control) | — | — | $1.8 \times 10^{14}$ | E |
| 122 (comparison) | II-1 | — | $2.0 \times 10^{13}$ | D |
| 123 (this invention) | II-1 | I-3 | $4.1 \times 10^{12}$ | A |
| 124 (this invention) | II-2 | I-5 | $3.8 \times 10^{12}$ | A |

Table 6 shows that the films containing both the alkyl betaine compound and the fluorinated anionic surfactant of formula (I) in the protective layers have significantly improved antistatic properties.

EXAMPLE 6

To a subbed polyethylene terephthalate film base, a photographic emulsion coating solution comprising a stabilizer and hardener incorporated in an X-ray photographic high-sensitivity emulsion containing 6% gelatin and 6% silver iodobromide (silver iodide: 1.5 mol%), and an aqueous coating solution for forming a surface protective layer that consisted of gelatin, water and a hardener and being free of an antistat were applied continuously and dried. For the compositions of the respective layers, see Table 7 below. The sample obtained was divided into six portions, which were separately immersed in 3% aqueous solutions of the compounds shown in Table 8 for 30 minutes. When the compounds were a mixture, Compound (II) was 70 wt% and Compound (I) was 30 wt% so that the concentration of the mixture was 3%. As a comparison, one of the samples was immersed in 3% aqueous saponin. The thus-treated samples were left to stand at 25° C. and 25% RH for 2 hours, and their surface resistivity was measured by the method described below. Static marking was checked as follows: a white rubber sheet was placed on a face of the sample and a rubber roller was rolled on the white rubber sheet to apply a constant friction under conditions at 25° C. and 40% RH. After removing the white rubber sheet, the sample was developed in a developer of the formulation indicated below, fixed and washed for checking the formation of static marks. The results of the two tests with each sample are set forth in Table 8.

Surface Resistivity

The sample was sandwiched between brass electrodes (electrode gap: 0.14 cm; length: 10 cm; the part in contact with the sample was made of stainless steel) and the one-minute value was read on an insulation resistance tester (Model: MM-V-M of Takeda Riken).

| Formulation of Developer | |
|---|---|
| Warm water (50° C.) | 700 ml |
| N—Methyl-p-aminophenol sulfate | 4 g |
| Anhydrous sodium sulfite | 60 g |
| Hydroquinone | 10 g |
| Sodium carbonate (monohydrate) | 53 g |
| Potassium bromide | 25 g |
| Water to make | 1 l |

TABLE 7

| | Composition of Coating Solution (per kg) | |
|---|---|---|
| | For Emulsion Layer | For Protective Layer |
| Binder | Gelatin 60 g | Gelatin 50 g |
| Silver | Silver iodobromide 60 g | — |
| Hardener | 2% Solution of Na salt of 2-hydroxy-4,6-dichloro-s-triazine 10 ml | 2% Solution of Na salt of 2-hydroxy-4,6-dichloro-s-triazine 10 ml |
| Stabilizer | 0.3% Solution of 1-phenyl-5-mercaptotetrazole 7 ml | — |
| Water | 880 ml | 950 ml |

(thickness: emulsion layer: 5μ, protective layer: 1μ)

TABLE 8

| | Comparison of Antistatic Properties | | |
|---|---|---|---|
| Sample | Antistat | Surface Resistivity (Ω) | Static Marking |
| 131 (comparison) | Compound (II-3) | $1.2 \times 10^{13}$ | D |
| 132 (this invention) | Compound (II-3) + Compound (I-3) | $2.1 \times 10^{12}$ | A |
| 133 (this invention) | Compound (II-3) + Compound (I-5) | $1.5 \times 10^{12}$ | A |
| 134 (this invention) | Compound (II-3) + Compound (I-9) | $1.7 \times 10^{12}$ | A |
| 135 (comparison) | Saponin | $10^{14}$ | D |
| 136 (control) | None | $10^{14}$ | E |

As Table 8 shows, few or no static marks were formed on the films (Samples (132), (133) and (134)) treated with the aqueous solution containing both the Compounds (I) and (II) of this invention, and their surface resistivity decreased significantly. A great number of static marks were formed on Sample (131) (containing the alkyl betaine Compound (II-3) only) and Sample (135) (containing saponin), and their surface resistivity decreased little. Blot-like static marks formed on Sample (136) throughout.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive element comprising a silver halide and containing in at least one photographic layer thereof a compound of formula (I)

$$MO_3S-CH_2-\underset{\underset{COOR_2}{|}}{CH}-CH_2-COOR_1 \quad (I)$$

wherein at least one of $R_1$ and $R_2$ is a fluorine-substituted alkyl group, and $R_1$ or $R_2$ can be a substituted or unsubstituted alkyl or aryl group, and M is a cation.

2. A photographic element as in claim 1 containing said compound of formula (I) in an outermost layer of said photographic material.

3. A photographic element as in claim 1 or 2, wherein the alkyl groups constituting $R_1$ and $R_2$ contain from 1 to 30 carbon atoms and the aryl groups constituting $R_1$ or $R_2$ are phenyl or naphthyl groups.

4. A photographic element as in claim 3, wherein the alkyl groups constituting $R_1$ and $R_2$ contain from 2 to 20 carbon atoms.

5. A photographic element as in claim 1 or 2, wherein the fluorine-substituted alkyl group is selected from $-(CH_2)_nC_mF_{2m+1}$, $-(CH_2)_n(CF_2)_mH$, $-(CH_2CH_2O)_{n1}(CH_2)_n-C_mF_{2m+1}$, $-(CH_2CH_2O)_{n1}(CH_2)_n(CF_2)_mH$, $-(CH_2)_{n1}NHCO(CF_2)_mH$, or $-(CH_2)_{n1}NHCOC_mF_{2m+1}$, wherein n is 0, 1 or 2, m is 1 to 12, and n1 is 1 to 4.

6. A photographic element as in claim 1 or 2, wherein M is cation ion selected from the group $Na^+$, $K^+$, $Ca^{++}$, $NH_4^+$, $C_2H_5-NH_3^+$, $HN(C_2H_5)_3^+$, or $H_3NCH_2CH_2OH^+$.

7. A photographic element as in claim 1 or 2, wherein said compound of formula (I) is present in said layer in an amount of from 0.05 to 50 mg/m².

8. A photographic element as in claim 1 or 2, wherein the fluorinated anionic surfactant of formula (I) is present in said layer in an amount of from 1 to 20 mg/m².

9. A photographic light-sensitive element comprising a silver halide and containing in at least one photographic layer thereof an alkyl betaine ion surfactant and a fluorinated anionic surfactant of formula (I)

$$MO_3S-CH_2-\underset{\underset{COOR_2}{|}}{CH}-CH_2-COOR_1 \quad (I)$$

wherein at least one $R_1$ and $R_2$ is a fluorine-substituted alkyl group, and $R_1$ or $R_2$ can be a substituted or unsubstituted alkyl or aryl group, and M is a cation.

10. A photographic element as in claim 9 containing said alkyl betaine surfactant and said fluorinated anionic surfactant of formula (I) in an outermost layer of said photographic material.

11. A photographic element as in claim 9 or 10, wherein alkyl groups constituting $R_1$ and $R_2$ contain from 1 to 30 carbon atoms and aryl groups constituting $R_1$ or $R_2$ are phenyl or naphthyl groups.

12. A photographic element as in claim 11, wherein alkyl groups constituting $R_1$ and $R_2$ contain from 2 to 20 carbon atoms.

13. A photographic material as in claim 9, wherein the fluorine-substituted alkyl group is selected from $-(CH_2)_nC_mF_{2m+1}$, $-(CH_2)_n(CF_2)_mH$, $-(CH_2CH_2O)_{n1}(CH_2)_nC_mF_{2m+1}$, $-(CH_2CH_2O)_{n1}(CH_2)_n(CF_2)_mH$, $-(CH_2)_{n1}(NHCO(CF_2)_mH$, or $-(CH_2)_{n1}NHCOC_mF_{2m+1}$ wherein n is 0, 1 or 2, m is 1 to 12, and n1 is 1 to 4.

14. A photographic material as in claim 9 or 10, wherein M is cation ion selected from the group $Na^+$, $K^+$, $Ca^{++}$, $NH_4^+$, $C_2H_5-NH_3^+$, $HN(C_2H_5)_3^+$, or $H_3NCH_2CH_2OH^+$.

15. A photographic material as in claim 9 or 10, wherein said alkyl betaine compound is selected from formulae (II) or (III)

$$RCONH(CH_2)_p-\overset{\oplus}{\underset{\underset{\underset{R_5}{|} \underset{R_6}{|}}{CH-(CH)_x-COO^{\ominus}}}{N}}-R_4 \quad (II)$$

$$R-\overset{\oplus}{\underset{\underset{\underset{R_5}{|} \underset{R_6}{|}}{CH-(CH)_x-COO^{\ominus}}}{N}}-R_4 \quad (III)$$

wherein R represents a saturated or unsaturated hydrocarbon group having from 7 to 21 carbon atoms; $R_3$ and $R_4$ each represents an alkyl group having from 1 to 18 carbon atoms, a hydroxyalkyl group, or a polyalkylene oxide group; $R_5$ and $R_6$ each represents hydrogen or an alkyl group having from 1 to 4 carbon atoms; p is an integer of at least 2; and x is 0 or 1.

16. A photographic material as in claim 9 or 10, wherein the fluorinated anionic surfactant of formula (I) is present in said layer in an amount of from 5 to 100 mg/m².

17. A photographic material as in claim 9 or 10, wherein the fluorinated anionic surfactant of formula (I) is present in said layer in an amount of from 20 to 50 mg/m².

18. A photographic material as in claim 9 or 10, wherein said alkyl betaine surfactant is present in said layer in an amount of from 10 to 500 mg/m².

19. A photographic material as in claim 9 or 10, wherein said alkyl betaine surfactant is present in said layer in an amount of from 30 to 100 mg/m².

20. A photographic material as in claim 15, wherein said alkyl betaine is present in an amount of from 10 to 500 mg/m².

21. A photographic material as in claim 15, wherein said alkyl betaine is present in an amount of from 30 to 100 mg/m².

* * * * *